United States Patent [19]

Pert et al.

[11] Patent Number: 5,534,495
[45] Date of Patent: Jul. 9, 1996

[54] TREATMENT OF NON-HIV NEUROPATHIC PAIN SYNDROMES

[75] Inventors: Candace B. Pert; Michael R. Ruff, both of Potomac, Md.

[73] Assignee: Advanced Peptides and Biotechnology Sciences, Sewickley, Pa.

[21] Appl. No.: 385,443

[22] Filed: Feb. 8, 1995

Related U.S. Application Data

[63] Continuation of Ser. No. 67,523, May 25, 1993, abandoned.

[51] Int. Cl.$^6$ .................................................. A61K 38/00
[52] U.S. Cl. ............................................. 514/16; 514/17
[58] Field of Search .................................... 514/16–17

[56] References Cited

U.S. PATENT DOCUMENTS

| | | |
|---|---|---|
| 3,531,258 | 9/1970 | Merrifield et al. |
| 5,063,206 | 11/1991 | Bridge et al. ........................ 514/16 |
| 5,446,026 | 8/1995 | Ruff et al. ........................... 514/15 |

OTHER PUBLICATIONS

Cecil Textbook of Medicine, 19th Edition, p. 2117–2124 and 2230–2236.

Neuropathic Pain Syndromes, Mitchell B. Max, Advances in Pain Research and Therapy, vol. 18, Raven Press, Ltd. New York 1991; pp. 193–219.

Peptide T Sequences Prevent Neuronal Cell Death Produced by the Envelope Protein (gp120) of the Human Immunodeficiency Virus, D. E. Brenneman, et al, Drug Development Research 15: 361–369 (1988).

Role of Peptide T in Palliation of HIV-1 Related Painful Peripheral Neuropathy, D. K. MacFadden, VII Internatl. Conference on AIDS, Florence 191, W.B. 2173.

HIV Envelope Protein–Induced Neuronal Damage and Retardation of Behavioral Development in Rat Neonates, Hill et al, Brain Research, 603 (1993) 222–23.

Society For Neuroscience Abstract, GP–120 Administered Intrathecally Induces Monoparesis in Rats, J. L. Steinman, et al, May 3, 1993.

*Primary Examiner*—Toni R. Scheiner
*Assistant Examiner*—Sheela J. Huff
*Attorney, Agent, or Firm*—McAulay Fisher Nissen Goldberg & Kiel

[57] ABSTRACT

The present invention relates to methods of treating diabetic and other non-HIV related neuropathic pain. The methods involve administration of an effective amount of defined linear peptides to patients. The peptides can be administered for example, as a powder or a solution obtained by dissolving a powder in a pharmaceutically acceptable solvent. Intranasal or sublingual administration of the defined peptides is the most preferred treatment.

18 Claims, 1 Drawing Sheet

TREATMENT OF NON-HIV NEUROPATHIC PAIN SYNDROMES

This is a continuation, of application Ser. No. 08/067,523, filed May 25, 1993, now abandoned.

BACKGROUND OF THE INVENTION

The invention relates to the use of defined linear peptides in the treatment of diabetic and other non-HIV neuropathic pain syndromes.

Several pain syndromes associated with disorders of the peripheral and central nervous system ("neuropathic pain") exist and few if any effective treatments for such pain are known.

Patients with such conditions make up a large proportion of those whose pain remains resistant to current therapies. Among the most common causes are the neuropathies associated with diabetes, cancer chemotherapy, herpes zoster, cervical or lumbar root compression owing to degenerative spine disease, malignant lesions of nerve plexus or root, nerve trauma, including amputation, HIV infection, and lesions of central pain pathways, including spinothalamic tract, thalamus, or thalamic radiations [Max, M. B., "Neuropathic Pain Syndromes", in *Advances in Pain Research and Therapy*, V18 (ed. M. Max et al) Raven Press, New York, 1991]. Drug-induced, or toxic, neuropathies have also been described. Thus the antivirals ddI and ddC commonly cause peripheral neuropathies, as do Vincristine (a cancer chemotherapeutic agent), Dilantin (a seizure medication), high dose vitamins, Isoniazid (a tuberculosis medication), and folic acid antagonists.

Patients' symptoms may include the unusual sensations of burning, tingling, electricity, pins and needles, stiffness, numbness in the extremities, feelings of bodily distortion, allodynia (pain evoked by innocuous stimulation of the skin), and hyperpathia (an exaggerated pain response persisting longs after pain stimuli cease).

The neuropathic pain syndromes result, apparently, from a variety of lesions and appear to encompass a mixed group of underlying physiological abnormalities. However, recent findings and treatment modalities have begun to suggest the existence of a common, unifying defect for a number of pain syndromes. As this may now be envisioned to occur, novel treatments which reverse or restore the normal functioning of the seemingly diverse lesions may be envisioned with efficacy against many diverse neuropathies.

The underlying basis for this new conception relates to evidence that a specific growth factor or neurotrophin, secreted by neurons, glia, neighboring parenchymal cells, or in endocrine fashion, is needed to support and maintain the normal functioning and viability of sensory neuronal pathways, either in the periphery or the brain. Pathologies caused by different mechanisms or etiologic agents, as detailed above, may have as a common convergence the loss or diminution of the needed neurotrophin. This then results in Wallerian type degeneration, nerve dystrophy or other dysfunctional or neurophysiological abnormality, the end result being hyperalgesia and enhanced pain nociception.

The synthesis of peptide T and its use in the treatment of mental disorders and memory deficits not caused by HIV infection has been disclosed in U.S. Pat. No. 5,063,206, the disclosure of which is incorporated herein by reference.

Recently it has been reported (Brenneman et al, Peptide T prevents gp120 induced neuronal cell death in vitro:relevance to AIDS dementia, *Drug Dev. Res.* 15:361–369, 1988.) that peptide T, which has structural relatedness to the neurotrophin vasoactive intestinal peptide (VIP), also will act to maintain the growth and viability of neurons in culture dishes. Structure-activity studies indicate that this activity of peptide T is due to a specific homology with VIP.

Additionally, peptide T has been reported to have benefit in the neurological pain (MacFadden et al, (abstr) Role of peptide T in palliation of HIV-1 related painful peripheral neuropathy, *VII Intnat ConfAIDS* (Firenze) 1991 #W.B.217) caused by HIV infection. However, unlike the treatment of diabetic and other non-HIV neuropathic pain syndromes, in the treatment of HIV-related painful peripheral neuropathy, the function of peptide T is to block the toxic actions of virally derived proteins on the nervous system.

SUMMARY OF THE INVENTION

It is an object of the present invention to provide a method for alleviating the symptoms of neuropathic pain, in whatever non-HIV clinical setting it may occur, by administering to a patient suffering from such symptoms an effective amount of a peptide capable of blocking the loss, destruction, or dysfunction of those cellular constituents which lead to non-HIV neuropathic pain.

It is another object of the present invention to treat patients suffering from neuropathic pain syndrome, other than HIV-related neuropathy, with an amount of defined linear peptides, including peptide T, sufficient to ameliorate the symptoms associated with the syndrome.

An additional object of the present invention is the use of intranasal therapy using defined linear peptides, including peptide T, which reduces the symptoms of diabetic and other non-HIV related neuropathic pain.

DETAILED DESCRIPTION OF THE INVENTION

Figure 1:
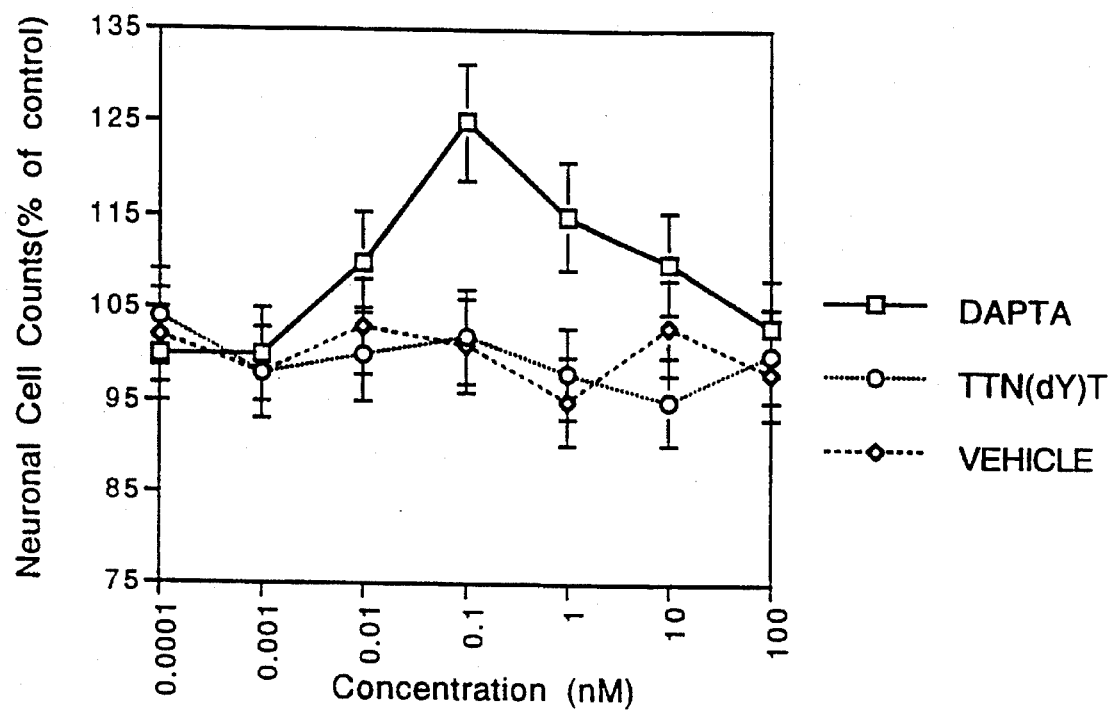
FIG. 1 is a graph illustrating the neuronal cell count of neuronal cell cultures treated for five days with an active peptide (DAPTA), an inactive peptide (TTN(dY)T), or a control (no peptide).

The class of compounds for use in the practice of the invention contain peptides of the formula (I):

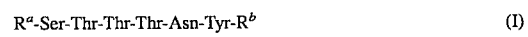

$$R^a\text{-Ser-Thr-Thr-Thr-Asn-Tyr-}R^b \qquad (I)$$

wherein $R^a$ represents an amino terminal residue which is Ala-, D-Ala, or Cys-Ala; and $R^b$ represents a carboxy terminal Thr-, Thr-amide, and derivatives thereof, such as esters and amides;

or a linear peptide of the formula (II):

$$R^1\text{-}R^2\text{-}R^3\text{-}R^4\text{-}R^5 \qquad (II)$$

wherein $R^1$ is an amino terminal residue which is X-R' or R' wherein R' is Thr-, Ser-, Asn-, Leu-, Ile-, Arg- or Glu- and X is Cys;

$R^2$ is Thr, Ser, or Asp;

$R^3$ is Thr, Ser, Ash, Arg, Gln, Lys or Trp;

$R^4$ is Tyr; and $R^5$ is preferably a carboxy terminal residue which is R"X or R" wherein R" may be any amino acid (Thr, Arg or Gly being preferred); or an ester or amide derivative thereof;

or a linear peptide of the formula (III):

$$R^{1'}\text{-}R^{2'}\text{-}R^{3'}\text{-}R^{4'}\text{-}R^{5'} \qquad (III)$$

wherein $R^{1'}$ is an amino terminal residue Ala-$R^1$, d-Ala-R' or X-Ala-R'; and $R^{5'}$ is a carboxy terminal residue or, preferably, an amide or ester derivative thereof;

or the physiologically acceptable salts of the peptides of formulas (I), (II) or (III).

While the preferred amino acids at $R^5$ and $R^{5'}$ have been designated, it is known that the amino acid at this position may vary widely. In fact, it is possible to terminate the peptide with $R^4$ (tyrosine) as the carboxy terminal amino acid wherein $R^5$ or $R^{5'}$ is absent. Such peptides retain the binding properties of the group taught herein. Serine and threonine appear to be interchangeable for purposes of biological properties taught herein. The active compounds of the invention may exist as physiologically acceptable salts of the peptides.

Most preferred peptides, as well as peptide T above, are the following octapeptides of formula (I):

D-Ala-Ser-Thr-Thr-Thr-Asn-Tyr-Thr, and D-Ala-Ser-Thr-Thr-Thr-Asn-Tyr-Thr-amide;

and the following pentapeptides of formula (II):

Thr-Asp-Asn-Tyr-Thr, Thr-Thr-Ser-Tyr-Thr, and Thr-Thr-Asn-Tyr-Thr and their analogues with D-Thr as the amino terminal residue and/or an amide derivative at the carboxy terminal.

The compounds of the invention may be beneficially modified by methods known to enhance passage of molecules across the blood-brain barrier. Acetylation has proven to be especially useful for enhancing binding activity of the peptide. The terminal amino and carboxy sites are particularly preferred sites for modification.

The peptides of this invention may also be modified in a constraining conformation to provide improved stability and oral availability. Unless otherwise indicated the amino acids are, of course, the natural form of L-stereoisomers.

The hereindescribed peptides were custom synthesized by Peninsula Laboratories under a confidentiality agreement between the inventors and the manufacturer. The Merrifield method of solid phase peptide synthesis was used. (See U.S. Pat. No. 3,531,258 which is incorporated herein by reference.) The synthesized peptides are especially preferred. While peptide T and the pentapeptide which is a portion thereof could be isolated, the peptides prepared in accordance with Merrifield are free of viral and cellular debris. Hence, untoward reactions due to contaminants does not occur when the synthesized peptides are used.

The peptides that are preferably to be administered intranasally or sublingually in accordance with the invention may be produced by conventional methods of peptide synthesis. Both solid phase and liquid phase methods, as well as other methods e.g., enzymatic methods, may be used. We have found the solid phase method of Merrifield to be particularly convenient. In this process the peptide is synthesized in a stepwise manner while the carboxy end of the chain is covalently attached to an insoluble support. During the intermediate synthetic stages the peptide remains in the solid phase and therefore can be conveniently manipulated. The solid support is a chloromethylated styrene-divinylbenzene copolymer.

An N-protected form of the carboxy terminal amino acid, e.g. a t-butoxycarbonyl protected (Boc-) amino acid, is reacted with the chloromethyl residue of the chloromethylated styrene divinylbenzene copolymer resin to produce a protected amino acyl derivative of the resin, where the amino acid is coupled to the resin as a benzyl ester. This is deprotected and reacted with the next required amino acid thus producing a protected dipeptide attached to the resin. The amino acid will generally be used in activated form, e.g. by use of a carbodiimide or active ester. This sequence is repeated and the peptide chain grows one residue at a time by condensation at the amino end with the required N-protected amino acids until the required peptide has been assembled on the resin. The peptide-resin is then treated with anhydrous hydrofluoric acid to cleave the ester linking the assembled peptide to the resin, in order to liberate the required peptide. Side chain functional groups of amino acids which must be blocked during the synthetic procedure, using conventional methods, may also be simultaneously removed. Synthesis of a peptide with an amide group on its carbons terminal can be carried out in a conventional manner, using a 4-methylbenzylhydroxylamine resin.

As an aspect of the invention, we provide a pharmaceutical composition comprising a peptide compound of the invention in association with pharmaceutically acceptable carrier or excipient, adapted for use in human or veterinary medicine. Such compositions may be presented for use in a conventional manner in admixture with one or more physiologically acceptable carriers or excipients. The compositions may optionally further contain one or more other therapeutic agents.

Thus, the peptides according to the invention may be formulated for oral, sub-lingual, intranasal, buccal, parenteral, topical or rectal administration.

In particular, the peptides according to the invention may be formulated for injection or for infusion and may be presented in unit dose form in ampoules or in multidose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form for constitution with a suitable vehicle, e.g., sterile, pyrogen-free water, before use. In particularly preferred embodiments, the active ingredient may be administered sub-lingually or intranasally, preferably in more than one daily application.

The pharmaceutical compositions according to the invention may also contain other active ingredients such as antimicrobial agents, or preservatives.

The compositions may contain from 0.001–99% of the active material.

The invention further provides a process for preparing a pharmaceutical composition which comprises bringing a peptide of the invention into association with a pharmaceutically acceptable excipient or carrier.

For administration by injection, nasal spray or infusion, the total daily dosage as employed for treatment of an adult human of approximately 70 kg body weight will range from about 0.02 to about 50 mg, typically from about 0.02 to about 30 mg, for example, from 0.02 mg to 10 mg. The total daily dosage may be administered in a single dosage application or in several dosage applications (e.g., 1 to 4 partial dosage applications), which combined, equal the total daily dosage, depending on the route of administration and the condition of the patient.

It was found that the affinity constants are similar to more potent than those of morphine. On the basis of this affinity, dosage of 0.33–0.0003 mg/kg per day was suggested. This has proven to be effective. A blood concentration $10^{-6}$ to $10^{-11}$ molar blood concentration is suggested. In monkeys 3 mg/kg per day achieves a serum concentration of $150 \times 10^{-9}$ M. This concentration is 15 times greater than necessary to achieve a concentration of $10^{-8}$ M. Primates generally require 10 times the dose used on humans.

Antigenic sequences from crab as well as proteins from other invertebrates can also be added to the peptides of the invention to promote antigenicity.

A preferred embodiment of the present invention comprises delivery of the short peptide sequence by sublingual or intranasal administration. The dosage levels of the peptides may vary, but generally are from about 0.2 to 50 mg/day, for example, about 0.2, 1.2, 6 or 30 mg/day, given sublingually or intranasally by metered spray, in three generally equally divided doses every eight hours.

In one embodiment, the peptides would be administered intermittently. In other words, a pharmaceutical composition containing the active peptide would be administered continually over a period of time, e.g. 2–3 months, whereafter the administration would be discontinued for a period of time, e.g. 2–3 months. In another embodiment, the dose of the active peptide would be varied over the course of administration. For example, a relatively higher dose, e.g. 6 mg/day, would be administered for a predetermined period of time, followed by administration of a relatively lower dose, e.g. 0.2 mg/day. The use of a peptide of the present invention, including peptide T, has no toxic effect on blood cell counts, EKG, blood chemistries or urinalysis. Intranasal or sublingual administration of a peptide according to the present invention is a preferred and safe therapeutic means for ameliorating the symptoms of diabetic and other non-HIV related neuropathic pain syndromes.

EXPERIMENTAL METHODS AND DATA

A) In vitro use of peptide T to promote neuronal survival

The neuroprotective and neurotropic actions of the herein defined peptides were determined by their effects upon fetal rodent neuronal cultures. More specifically, dissociated hippocampal and/or cortical cultures were prepared from 2-day-old rat neonates (Sprague-Dawley rats) by previously described methods (Brenneman et al, Peptide T prevents gp120 induced neuronal cell death in vitro:relevance to AIDS dementia, *Drug Dev, Res.* 15:361–369, 1988), with the modification that rat neonates rather than mouse embryo's were the source of the brain tissue for the cultures. The dissociated cells were be plated at low density (50,000 cells/35-mm dish) upon confluent layers of astrocytes. The astrocyte feeder layers were prepared from the hippocampi and/or cortices of 2-day-old rat pups. Following treatment with 0,125% trypsin for 15 min, the tissue was triturated and plated at $2.5 \times 10^5$ cells into 35-mm tissue culture dishes coated with Vintrogen (Collagen, Palo Alto) and poly-L-lysine ($M_1$30–70K $10_{-5}$ M borate, pH 8.4, Sigma). The resulting feeder layers were grown in Eagle's minimal essential medium (MEM, formula 82-0234, Gibco) with 10% fetal bovine serum until confluent (12–14 days); feeder layers prepared in this way were devoid of neurons and consisted predominantly of flat cells that were stained by antibodies to glia fibrillary acidic protein. When hippocampal and/or cortical neurons were added to the confluent feeder cultures, the medium was changed to 94% MEM, 5% horse serum (Gibco) and an added nutrient supplement containing insulin, transferrin, putrescine, selenium, corticosterone, progesterone and triiodothyronine. The resulting mixed neuron/glia cultures are treated one day after plating with 5'-fluoro-2'-deoxyuridine (15 μg/ml plus uridine, 35Mg/ml) to suppress the overgrowth of background cells. The neuronal cultures were allowed to grow for one week prior to the beginning of the experimental period and the medium was changed prior to adding peptides or controls.

B) Neuronal survival assay in vitro

Dilutions of peptide T or analogs were added to 7-day-old neuronal cultures. The test period of exposure to peptides was five days long, a period in which cell survivability can be accurately quantitated. At the end of the test period, neurons were identified immunocytochemically with antisera to neuron-specific enolase. Neurons were counted in 100 fields at predetermined stage coordinates. Cultures were coded and counted in a blinded fashion without knowledge of sample treatment. The total area counted was 50 mm$^2$. (% survival=# cells experimental/control x100), equivalent to 100 fields. Each value reported is the mean of six separate dishes. Error bars represent the standard error of the mean and analysis of variance was by Student-Keuls multiple comparison of means. The Control culture has neuron counts that ranged from 750–1000 cells per 50 mm$^2$. The results of the 5-day neuronal cell survival tests are presented in FIG. 1, wherein the neuronal cell counts (as a percentage of Control) are shown graphically as a function of the concentration of the various peptides or Control being tested. It can be seen that over the concentration range of 10.0 to 0.01 nM an active peptide as contemplated by the present invention (D-ala 1-peptide T-amide, DAPTA) caused an increase in neuronal survival. The maximum effect was detected at 0.1 nM, with approximately a 25% increase in cell survival compared to vehicle (Control) treated cultures. An inactive peptide T analog with a D-tyrosine substitute [TTN(dY)T] did not cause this increase, nor did the vehicle control. By these results the active peptide (DAPTA) was shown to be, by itself, a neurotrophin for rat cortical neurons as their survival in culture after five days was significantly greater than vehicle treated cultures.

The beneficial effect was shown to be receptor mediated and specific as it occurred for an active peptide T analog but not and inactive one, and the effect was shown to be potent as it occurs at low concentrations. The bi-phasic nature of the response showed that the dose response curve for neuronal cell death in dissociated hippocampal and/or cortical neurons was generally V-shaped. The reasons for the biphasic nature of this response are unclear, but they may include one or more of the following: particle agonist-antagonist properties, activation of another receptor, down-regulation of receptors at high doses, or ligand self-association at high concentration.

Figure 2:
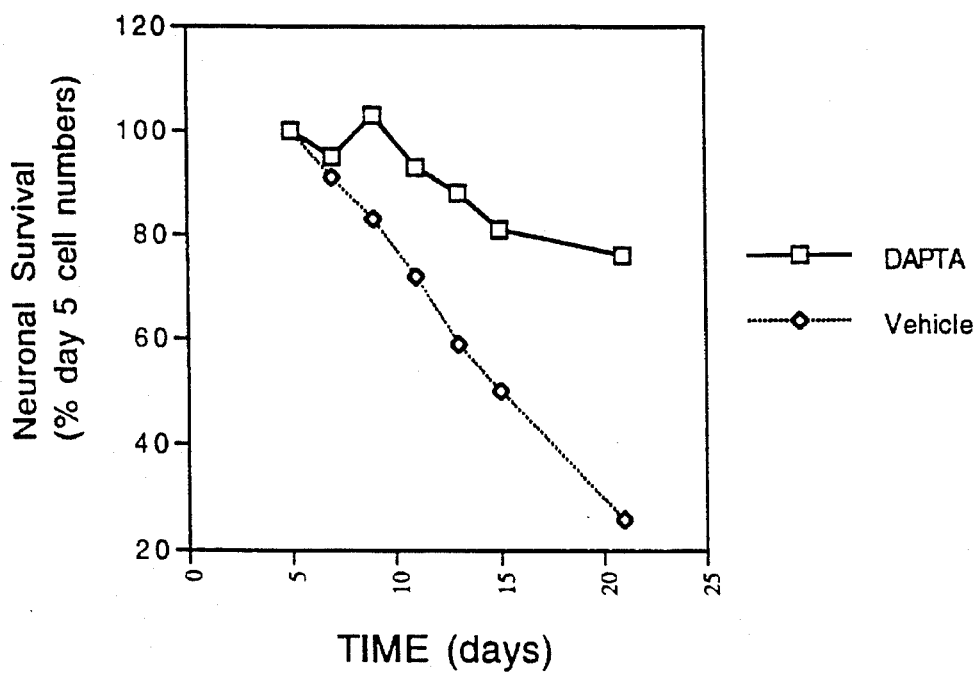
FIG. 2 is a graph comparing the duration of survival of hippocampal neuronal cell cultures maintained in the presence of an active peptide (DAPTA) or in the presence of a control (vehicle containing no peptide).

A comparison of neuronal survival, based on the percentage of the five-day survival count illustrated in FIG. 1, was made for cultures of hippocampal neuronal cells maintained for twenty one days either in the presence of active peptide (DAPTA) or in the presence of vehicle alone (Control). The results of this comparison are illustrated in FIG. 2, wherein the percentage of neuronal survival (based on the cell count at 5 days) is plotted as the ordinate and the time of treatment, in days, is plotted as the abscissa. Reference to FIG. 2 clearly indicates that treatment of hippocampal neurons in culture with D-Ala-peptide T amide (DAPTA) at 0.1 nM resulted in a 4-fold increase in cell survival after twenty one days compared to vehicle treated cultures and that at all times during the twenty one day test period cell survival rate was enhanced for DAPTA-treated cells. Thus it can be concluded that the normal apoptosis and cell death which occurs in the cultures can be substantially inhibited by addition of the hereindescribed peptides which promote neuron survival, a hallmark of a neurotrophic agent.

The above in vitro assay of neuropathic activity is well correlated with in vivo effect. Thus several recent publications indicate that peptide T and related structures, whose activity was first described based upon in vitro methods such as that described in herein, are able to support the growth and arborization of rodent cortical neurons as determined by Gogli and other histochemical staining methods (see Hill et al, HIV Envelope Protein-Induced Neuronal Damage and Retardation of Behavioral Development in Rat Neonates, *Brain Research,* Vol. 603, pages 222–233 (1993)). Additional evidence shows that peptide T and related peptides support growth of cortical and other neurons when injected into animals (see Socci et al, Chronic Peptide T Administration Prevents Neurocortical Atrophy Resulting From Nucleus Basalis Lesions in Age Rats, *Society For Neuroscience Abstracts,* Vol 18, Abstract No. 489.13 (1992)), which describes the use of peptide T to block the attrition of neurons as a part of normal aging, an in vivo neurotrophic effect, first described by in vitro observations such as those illustrated in FIGS. 1 and 2 herein.

C) Alleviation of neuropathic pain in a person with diabetes

A 62 year old male patient suffering from severe type II adult onset diabetes for over 10 years and having symptoms of severe diabetic peripheral neuropathy for over three years was treated by administering intranasal peptide T at a rate of 6 mgs per day in three evenly divided doses. After only one day, the patient could feel the sheets around his feet which had been completely numb and without feeling previously. In addition, of four extremely tender and highly infected sores on the soles of his feet, two had completely healed up after twelve weeks of peptide T treatment, and the two remaining sores were completely uninfected, much less tender, and were progressing to healing. Also, the patient, who had not walked for several years because of the extreme pain of the neuropathy in his legs and feet, was able to walk to work some 10 blocks each way every day after only a few weeks of treatment with peptide T. The patient also indicated that his extreme itchiness, the "pruritus" characteristic of diabetes, that used to bother him around the waistband of his pants vanished after 2 weeks of using peptide T, even though he had tried many different remedies over the years without noticing any significant relief.

What is claimed is:

1. A method for treating non-HIV related neuropathic pain syndrome in mammals which comprises administering an effective amount of a peptide of the formula (I):

$$R^a\text{-Ser-Thr-Thr-Thr-Asn-Tyr-}R^b \quad (I)$$

wherein $R^a$ represents an amino terminal residue which is Ala-, D-Ala, or Cys-Ala; and $R^b$ represents a carboxy terminal Thr- or Thr-amide an ester or amide derivative thereof, or a linear peptide of the formula (II):

$$R^1\text{-}R^2\text{-}R^3\text{-}R^4\text{-}R^5 \quad (II)$$

wherein $R^1$ is an amino terminal residue which is X-R' or R' wherein R' is Thr-, Ser-, Asn-, Leu-, Ile-, Arg- or Glu- and X is Cys;

$R^2$ is Thr, Ser, or Asp;

$R^3$ is Thr, Ser, Asn, Arg, Gln, Lys or Trp;

$R^4$ is Tyr; and $R^5$ is a carboxy terminal residue which is R"X or R' wherein R" may be any amino acid or an ester or amide derivative thereof;

or a linear peptide of the formula (III):

$$R^{1'}\text{-}R^2\text{-}R^3\text{-}R^4\text{-}R^{5'} \quad (III)$$

wherein $R^{1'}$ is an amino terminal residue Ala-$R^1$d-Ala-R' or X-Ala-R'; and $R^{5'}$ is a carboxy terminal residue or an amide or ester derivative thereof;

or the physiologically acceptable salts of a peptide of formulas (I), (II) or (II).

2. The method according to claim 1, which comprises administering an effective amount of a peptide of the formula (II) wherein $R^5$ is Thr, Arg or Gly; or a physiologically acceptable salt thereof.

3. The method according to claim 1, which comprises administering an effective amount of a peptide of the formula (III) or a physiologically acceptable salt thereof.

4. The method according to claim 1, which comprises administering an effective amount of a peptide of the formula (I) or a physiologically acceptable salt thereof.

5. The method according to claim 4 wherein said peptide of formula (I) is selected from D-Ala-Ser-Thr-Thr-Thr-Asn-Tyr-Thr, and D-Ala-Ser-Thr-Thr-Thr-Asn-Tyr-Thr-amide;

and physiologically acceptable salts thereof.

6. The method of claim 2, wherein said peptide of formula II is selected from

Thr-Asp-Asn-Tyr-Thr, Thr-Thr-Ser-Tyr-Thr, and Thr-Thr-Asn-Tyr-Thr;

and physiologically acceptable salts thereof.

7. The method claim 1 wherein said peptide is administered intranasally or sublingually.

8. The method claim 2 wherein said peptide is administered intranasally or sublingually.

9. The method claim 3 wherein said peptide is administered intranasally or sublingually.

10. The method claim 4 wherein said peptide is administered intranasally or sublingually.

11. The method claim 5 wherein said peptide is administered intranasally or sublingually.

12. The method claim 6 wherein said peptide is administered intranasally or sublingually.

13. The method according to claim 1 wherein said peptide is administered intranasally, daily, in three substantially equally spaced applications, the combined daily applications containing a total of from about 0.02 to 50 mg of said peptide.

14. The method according to claim 13 wherein the combined application contains about 1.2 mg of said peptide.

15. The method according to claim 13 wherein the combined application contains about 6 mg of said peptide.

16. The method according to claim 13 wherein the combined application contains about 30 mg of said peptide.

17. The method according to claim 13 wherein the combined application contains about 0.2 mg of said peptide.

18. A method for treating non-HIV related neuropathic pain syndrome in mammals which comprises administering an effective amount of D-Ala-Ser-Thr-Thr-Thr-Asn-Tyr-Thr-amide and physiologically acceptable salts thereof to the mammal.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( C ) STRANDEDNESS: unknown
        ( D ) TOPOLOGY: unknown ( i i ) MOLECULE TYPE: peptide ( i x ) FEATURE:
        ( A ) NAME/KEY: Peptide
        ( B ) LOCATION: 1
        ( D ) OTHER INFORMATION: /product="OTHER"
            / label=Ra
            / note="may be nothing"

( i x ) FEATURE:
        ( A ) NAME/KEY: Peptide
        ( B ) LOCATION: 1..2
        ( D ) OTHER INFORMATION: /product="OTHER"
            / label=Ra
            / note="may be Cys-Ala"

( i x ) FEATURE:
        ( A ) NAME/KEY: Peptide
        ( B ) LOCATION: 2
        ( D ) OTHER INFORMATION: /product="OTHER"
            / label=Ra
            / note="may be Ala or D-Ala"

( i x ) FEATURE:
        ( A ) NAME/KEY: Peptide
        ( B ) LOCATION: 9
        ( D ) OTHER INFORMATION: /product="OTHER"
            / label=Rb
            / note="may be carboxy terminal Thr"

( i x ) FEATURE:

( A ) NAME/KEY: Peptide
                ( B ) LOCATION: 9..10
                ( D ) OTHER INFORMATION: /product="OTHER"
                        / label=Rb
                        / note="may be Thr-amide, an ester or amide
                                derivative thereof"

( i x ) FEATURE:
                ( A ) NAME/KEY: Peptide
                ( B ) LOCATION: 10
                ( D ) OTHER INFORMATION: /product="OTHER"
                        / label=Rb
                        / note="may be nothing"

( x i ) SEQUENCE DESCRIPTION: SEQ ID NO:1:

Xaa  Xaa  Ser  Thr  Thr  Thr  Asn  Tyr  Xaa  Xaa
    1                   5                        1 0

( 2 ) INFORMATION FOR SEQ ID NO:2:

( i ) SEQUENCE CHARACTERISTICS:
                ( A ) LENGTH: 7 amino acids
                ( B ) TYPE: amino acid
                ( C ) STRANDEDNESS: unknown
                ( D ) TOPOLOGY: unknown ( i i ) MOLECULE TYPE: peptide ( i x ) FEATURE:
                ( A ) NAME/KEY: Peptide
                ( B ) LOCATION: 1..2
                ( D ) OTHER INFORMATION: /product="OTHER"
                        / label=R1
                        / note="an amino terminal residue which is Cys-R',
                                wherein R'is Thr, Ser, Asn, Leu, Ile, Arg,
                                or Glu"

( i x ) FEATURE:
                ( A ) NAME/KEY: Peptide
                ( B ) LOCATION: 3
                ( D ) OTHER INFORMATION: /product="OTHER"
                        / label=R2
                        / note="is Thr, Ser, or Asp"

( i x ) FEATURE:
                ( A ) NAME/KEY: Peptide
                ( B ) LOCATION: 4
                ( D ) OTHER INFORMATION: /product="OTHER"
                        / label=R3
                        / note="is Thr, Ser, Asn, Arg, Gln, Lys or Trp"

( i x ) FEATURE:
                ( A ) NAME/KEY: Peptide
                ( B ) LOCATION: 5
                ( D ) OTHER INFORMATION: /product="OTHER"
                        / label=R4
                        / note="is Tyr"

( i x ) FEATURE:
                ( A ) NAME/KEY: Peptide
                ( B ) LOCATION: 6..7
                ( D ) OTHER INFORMATION: /product="OTHER"
                        / label=R5
                        / note="is a carboxy terminal residue which is R''X
                                or R'', wherein R''may be any amino acid or
                                an ester or amide derivative thereof"

( i x ) FEATURE:
                ( A ) NAME/KEY: Peptide
                ( B ) LOCATION: 1
                ( D ) OTHER INFORMATION: /product="OTHER"
                        / label=R1
                        / note="may be nothing"

( i x ) FEATURE:
                ( A ) NAME/KEY: Peptide
                ( B ) LOCATION: 2
                ( D ) OTHER INFORMATION: /product="OTHER"

/ label=R1
/ note="may be Thr, Ser, Asn, Leu, Ile, Arg, or Glu"

( x i ) SEQUENCE DESCRIPTION: SEQ ID NO:2:

```
Xaa  Xaa  Xaa  Xaa  Xaa  Xaa  Xaa
1                    5
```

( 2 ) INFORMATION FOR SEQ ID NO:3:

( i ) SEQUENCE CHARACTERISTICS:
        ( A ) LENGTH: 7 amino acids
        ( B ) TYPE: amino acid
        ( C ) STRANDEDNESS: unknown
        ( D ) TOPOLOGY: unknown ( i i ) MOLECULE TYPE: peptide ( i x ) FEATURE:
        ( A ) NAME/KEY: Peptide
        ( B ) LOCATION: 1..3
        ( D ) OTHER INFORMATION: /product="OTHER"
            / label=R1'
            / note="is an amino terminal residue X-Ala-R'wherein
                      X is Cys and R'is Thr, Ser, Asn, Leu, Ile, Arg,
                      or Glu"

( i x ) FEATURE:
        ( A ) NAME/KEY: Peptide
        ( B ) LOCATION: 4
        ( D ) OTHER INFORMATION: /product="OTHER"
            / label=R2
            / note="is Thr, Ser, or Asp"

( i x ) FEATURE:
        ( A ) NAME/KEY: Peptide
        ( B ) LOCATION: 5
        ( D ) OTHER INFORMATION: /product="OTHER"
            / label=R3
            / note="is Thr, Ser, Asn, Arg, Gln, Lys, or Trp"

( i x ) FEATURE:
        ( A ) NAME/KEY: Peptide
        ( B ) LOCATION: 7
        ( D ) OTHER INFORMATION: /product="OTHER"
            / label=R5'
            / note="is a carboxy terminal residue or an amide
                      or ester derivative thereof"

( i x ) FEATURE:
        ( A ) NAME/KEY: Peptide
        ( B ) LOCATION: 1
        ( D ) OTHER INFORMATION: /product="OTHER"
            / label=R1'
            / note="is nothing"

( i x ) FEATURE:
        ( A ) NAME/KEY: Peptide
        ( B ) LOCATION: 2..3
        ( D ) OTHER INFORMATION: /product="OTHER"
            / label=R1'
            / note="is Ala-R'or d-Ala-R', wherein R'is Thr,
                      Ser, Asn, Leu, Ile, Arg, or Glu"

( x i ) SEQUENCE DESCRIPTION: SEQ ID NO:3:

```
Xaa  Xaa  Xaa  Xaa  Xaa  Tyr  Xaa
1                    5
```

( 2 ) INFORMATION FOR SEQ ID NO:4:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( i i ) MOLECULE TYPE: peptide (x i) SEQUENCE DESCRIPTION: SEQ ID NO:4:

Thr Asp Asn Tyr Thr
1               5

(2) INFORMATION FOR SEQ ID NO:5:

(i) SEQUENCE CHARACTERISTICS:
      (A) LENGTH: 5 amino acids
      (B) TYPE: amino acid
      (C) STRANDEDNESS: Not Relevant
      (D) TOPOLOGY: Not Relevant (i i) MOLECULE TYPE: peptide (x i) SEQUENCE DESCRIPTION: SEQ ID NO:5:

Thr Thr Ser Tyr Thr
1               5

(2) INFORMATION FOR SEQ ID NO:6:

(i) SEQUENCE CHARACTERISTICS:
      (A) LENGTH: 5 amino acids
      (B) TYPE: amino acid
      (C) STRANDEDNESS: Not Relevant
      (D) TOPOLOGY: Not Relevant (i i) MOLECULE TYPE: peptide (x i) SEQUENCE DESCRIPTION: SEQ ID NO:6:

Thr Thr Asn Tyr Thr
1               5